Figure 1:
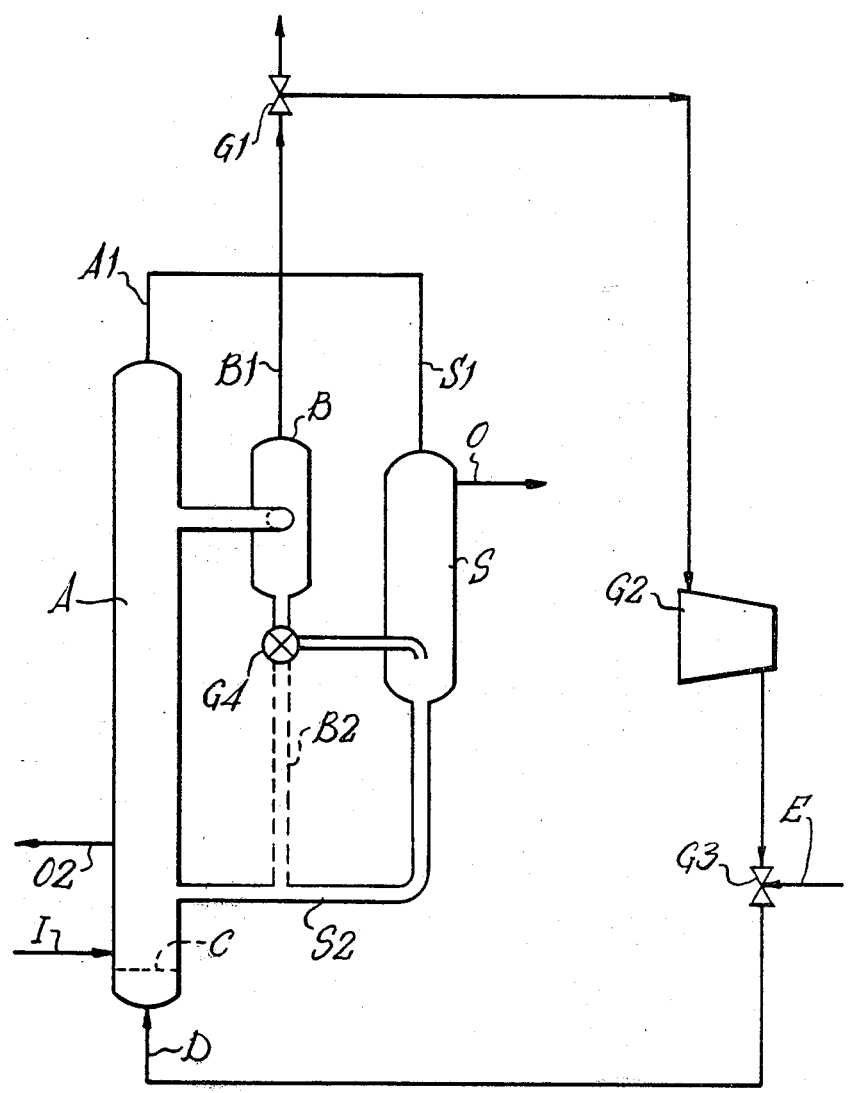

United States Patent [19]

Bu'Lock

[11] 4,357,424
[45] Nov. 2, 1982

[54] PROCESS FOR THE CONTINUOUS PRODUCTION OF FERMENTATION ALCOHOL

[75] Inventor: John D. Bu'Lock, Marple, England

[73] Assignee: Sim-Chem Limited, Cheshire, England

[21] Appl. No.: 212,125

[22] Filed: Dec. 2, 1980

[30] Foreign Application Priority Data

Dec. 13, 1979 [GB] United Kingdom ............... 7943065

[51] Int. Cl.³ .................... C12P 7/06; C12M 1/08
[52] U.S. Cl. .................................. 435/162; 435/161; 435/314
[58] Field of Search ............... 435/161, 162, 163, 164, 435/165, 315, 314, 313

[56] References Cited

U.S. PATENT DOCUMENTS 2,083,348  6/1937  Scholler et al. .................. 435/314

FOREIGN PATENT DOCUMENTS 366753  2/1932  United Kingdom ............... 435/315

Primary Examiner—Raymond N. Jones
Assistant Examiner—John E. Tarcza
Attorney, Agent, or Firm—LeBlanc, Nolan, Shur & Nies

[57] ABSTRACT

A process for the continuous production of fermentation alcohol, by effecting fermentation of a continuous or substantially continuous supply of the liquid substrate by a dense suspension of a suitable micro-organism in a reaction column wherein the suspension is maintained in a well mixed state. The mixture passes from the upper region of the reaction column into a degassing zone where less turbulent conditions readily permit degassing of the mixture, causing part of the degassed mixture to flow into a settling zone wherein quiescent conditions permit the biomass to settle out. The settled biomass is returned to the bottom of the reaction column to assist in the continuation of the fermentation process. Gases evolving from the top of the reaction column and from the tops of the degassing and settling zones are removed. At least a portion of the evolved gases are reintroduced into the bottom of the reaction column to maintain the well mixed state therein, and clarified liquor containing alcohol is removed from the top of the settling zone.

9 Claims, 2 Drawing Figures

PROCESS FOR THE CONTINUOUS PRODUCTION OF FERMENTATION ALCOHOL

This invention relates to a process for the continuous production of fermentation alcohol. The process requires little or no oxygen and maintains the treatment liquor in a uniformly mixed condition thus promoting the continuous growth of active biomass in the treatment system.

The process is particularly, though by no means exclusively, concerned with the fermentation of glucose solutions by yeasts to give ethanol and carbon dioxode.

According to the present invention there is provided a process for the continuous production of fermentation alcohol, including the steps of effecting fermentation of a substantially continuous supply of a liquid substrate by a dense suspension of a suitable micro-organism in a reaction column wherein the suspension is maintained in a well mixed state, causing the liquid/biomass mixture in an upper region of the column to pass into a degassing zone wherein less turbulent conditions readily permit degassing of the mixture, causing at least a part of the degassed mixture to flow from the degassing zone into a settling zone wherein quiescent conditions permit the biomass to settle out, returning the settled biomass to a lower region of the reaction column to assist in the continuation of the fermentation process, removing evolved gases from the upper end of the reaction column and from the degassing zone, reintroducing at least a portion of said evolved gases into the lower region of the reaction column thus to maintain said well mixed state therein, and removing from the settling zone clarified liquor containing product alcohol.

An embodiment of the invention will now be described, by way of example only, with reference to the apparatus used for carrying out the process as illustrated schematically in the accompanying drawings.

Figure 2:
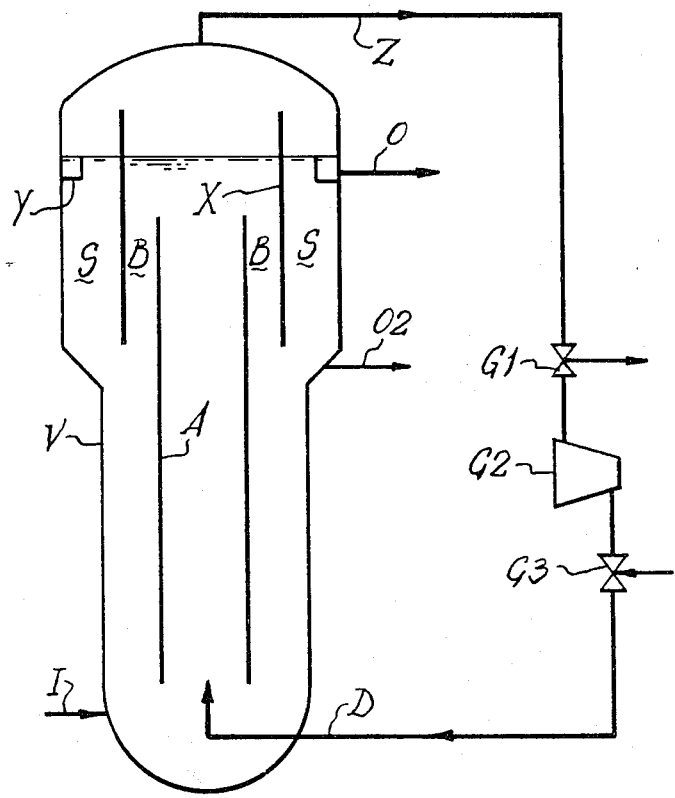

Of the drawings:

FIG. 1 is a diagrammatic illustration of one form of apparatus to carry out the process;

and FIG. 2 is a modified form of such apparatus.

The apparatus generally comprises a reaction vessel A of high aspect ratio connected near its upper end to a degassing vessel B which is similar in cross-section to the vessel A.

The reaction vessel A is equipped with a gas diffuser or sparge C in the lower region of the vessel, and a gas input line D beneath the sparge C. The upper ends of the vessels A and B communicate with gas or vapour lines A and B which join together and, via a pressure regulator G1 lead either to waste or two a compressor G2. The output of the compressor G2 is connected via an adjustable valve G3 to the line D feeding gas to the base of the reaction vessel A. A feed line E is also connected to the valve G3 to permit the introduction into the line D of air or other treatment gas, whereby the resultant gas mixture is arranged to pass into the reaction vessel A.

A settling vessel S is connected to the degassing vessel B at its lower end, and the lower end of the vessel S is connected by a line S2 to the lower end region of the reaction vessel A above sparge C. A line S1 is provided for the removal from vessel S of evolved gases and/or vapours, and this is connected to lines A and B. A line B2, shown in broken lines, connects the bottom end of vessel B to line S2. A valve G4 is preferably connected between vessel B and the vessel S, allowing adjustment of the proportion of the stream flowing through B which passes to the vessel S. Alternatively, the line B2 may be omitted altogether so that the entire return flow to vessel A is by way of vessel S.

An input line I is connected near the base of the reaction vessel A to introduce the substrate for the process. An output O is provided near the upper end of the vessel S to permit liquor containing product alcohol to be taken from the system. An output line O2 for a purpose to be described is connected to the lower region of vessel A.

The method in accordance with the invention can be carried out using the described apparatus in the following manner. In the particular instance of an ethanol/yeast fermentation, the process is initiated by filling the system with a process medium such as water and glucose, and this medium is inoculated with a yeast suspension, for example, by way of line I. Initially, a supply of air alone is introduced at line E via valve G3 and into line D for injection into the reacton vessel A. Fermentation commences, and the culture is maintained in this manner until an adequate population of aerobically grown yeast has developed in the vessel A, at which time the valve G3 is adjusted so that the air supply is largely replaced by carbon dioxide being recycled by the compressor G2 from the upper ends of vessels A, B and S. A small proportion of air is advantageously retained, since the ethanol/yeast fermentation is, strictly, microaerobic rather than truly anaerobic. In cases where the fermentation is effected with a strictly anaerobic microorganism, a different procedure will be necessary in which the initial supply of gas is of some inert gas such as nitrogen or carbon dioxide, or a mixture of such, from an external source, and this will be replaced as soon as possible by the recycled gases generated in the fermentation process.

Once the system is running as described, then a continuous supply and removal of media at an appropriate rate may be established.

As will be seen, therefore, in operation of the process the introduction of substrate at line I into the vessel A is continuous, and the liquid/biomass mixture passes progressively into the degassing vessel B. In the degassing stage of the process, conditions exist which are less turbulent than those in the reaction vessel A, and there is present a relatively low availability of the original substrate, so that the production of carbon dioxide by the biomass is reduced and the conditions permit the residual gas to be given off thus promoting separation of the degassed biomass from the fermented liquor owing to the relative specific gravities thereof.

Thus a part or the whole of the descending degassed biomass, and the liquid phase surrounding same, passes into the settling vessel S where the direction and magnitude of the liquor flow towards the outlet O permits the suspended biomass to settle out and so return via line S2 to the reaction vessel A to assist in maintaining the fermentation process. Adjustment of the valve G4 allows the proportion of mixture flowing through B2 and S2 to be varied, thus providing the optimum velocity through S for biomass separation.

The provision of the settling vessel S in addition to the degassing vessel B enables a substantially complete separation of the degassed biomass from the fermented liquor. In some cases, the efficiency of biomass return is so high that the biomass in the system accumulates to an unmanageable level, and a controlled continuous or intermittent removal thereof can be effected via line O2.

The recycling of the biomass in the system together with the continuous introduction of the substrate, and the reintroduction of fermentation gases at line D serve to maintain the treatment media in the vessel A, in a well mixed state thus promoting the growth of active biomass, as well as the fermentation process as a whole.

Referring now to FIG. 2 where parts having a like function are denoted by the same reference characters as those used in FIG. 1, it will be seen that there is provided a common vessel V in which is disposed a cylindrical reaction column A and a concentric cylindrical baffle X surrounding the column A, an annular weir Y surrounding the baffle X and attached to the inner surface of the wall of the vessel V. In this example, the liquid/biomass mixture in the upper region of the column A is caused to flow down through the annular degassing zone B where less turbulent conditions permit the degassing of the mixture, and the gas is removed via line Z connected to the top of the vessel V. Of the mixture passing downwardly in zone B a portion flows upwardly into the annular settling zone S and is removed via weir Y to outlet line O. The increased volume of settling zones with respect to zone B permits the biomass to settle out leaving relatively clear liquor to pass over the weir Y. The descending stream of liquid/diomass mixture re-enters the base of the column A to maintain the process, this being assisted by the introduction of recycled gas at line D introduced by the controlling effects of valves G1 and G3 and compressor G2. The embodiment of FIG. 2 whilst functionally similar to that of FIG. 1, is constructed in a more suitable manner in the interests of economy and space.

In cases where the product alcohol is itself inhibitory to the progress of the fermentation it may be necessary for the inhibitory product to be continuously, and selectively, removed from the fermentation liquor in the system.

It will be seen that the process according to the invention enables substantial productivity benefits to be achieved by the increased concentration of biomass in the fermentation system and this is attained by simple means in an enclosed system, without the use of pumps or centrifuges or other mechanical devices and without the dangers of excessive solids accumulation in so-called 'dead spots' where liquid flow might otherwise be impeded. It is expected that considerable biomass concentrations can be achieved yet still maintained in a well mixed condition so far as the main body of the fermentation liquor is concerned.

What is claimed is:

1. A process for the continuous production of fermentation alcohol, comprising the steps of effecting fermentation of a substantially continuous supply of a liquid substrate by a dense suspension of a suitable microorganism in a reaction column wherein the suspension is maintained in a well mixed state, thereby producing a liquid/biomass mixture, causing said mixture in an upper region of the column to pass into a degassing zone wherein less turbulent conditions readily permit degassing of the mixture, causing at least a part of the degassed mixture to flow from the degassing zone into a settling zone wherein quiescent conditions permit the biomass to settle out, returning substantially all of the settled biomass to a lower region of the reaction column and reintroducing it into the fermentation process therein to maintain the process, removing evolved gases from the upper end of the reaction column and from the degassing zone, reintroducing at least a portion of said evolved gases into the fermentation process in the lower region of the reaction column thus to maintain said well mixed state therein, and removing from the settling zone clarified liquor containing product alcohol.

2. A process according to claim 1, wherein the liquid substrate is introduced into the reaction column in the lower region thereof, and the degassed mixture enters the settling zone in the lower region thereof.

3. A process according to claim 1, wherein evolved gases are removed from the settling zone.

4. A process according to claim 1, wherein the proportion of the degassed mixture from the degassing zone which enters the settling zone is variable and controlled, any mixture not entering the settling zone, being returned to the reaction column together with said settled biomass.

5. A process according to claim 1, wherein a further treatment gas is introduced into the lower region of the reaction column together with said evolved gases.

6. A process according to claim 5, wherein said other treatment gas is air, and the proportion thereof is adjustable.

7. A process according to claim 1, wherein biomass is continuously removed at a controlled rate from said reaction column.

8. A process according to claim 1, wherein any product such as product alcohol which is inhibitory to the process, is continuously or selectively removed from the fermentation liquor in the system.

9. A process according to claim 1, wherein biomass is intermittently removed at a controlled rate from said reaction column.

* * * * *